United States Patent [19]

Jegham et al.

[11] Patent Number: 5,434,169

[45] Date of Patent: Jul. 18, 1995

[54] PIPERIDINE DERIVATIVES, THEIR PREPARATION AND THEIR APPLICATION IN THERAPY

[75] Inventors: Samir Jegham, Argenteuil; Itzchak Angel, Rungis; Thomas Purcell, Montford L'Amaury; Johannes Schoemaker, Gif S/Yvette, all of France

[73] Assignee: Synthelabo, Le Plessis Robinson, France

[21] Appl. No.: 127,078

[22] Filed: Sep. 27, 1993

[30] Foreign Application Priority Data

Sep. 28, 1992 [FR] France .................. 92 11551

[51] Int. Cl.$^6$ .................. A61K 31/445; C07D 401/04
[52] U.S. Cl. ...................... 514/322; 514/300; 514/323; 514/326; 546/121; 546/199; 546/201; 546/210
[58] Field of Search ............... 546/121, 199, 201, 210; 514/300, 322, 323, 326

[56] References Cited

U.S. PATENT DOCUMENTS

| | | | |
|---|---|---|---|
| 4,707,487 | 11/1987 | Arrang | 514/326 |
| 4,925,851 | 5/1990 | Houlihan | 514/326 |
| 5,008,390 | 4/1991 | Bender | 546/199 |
| 5,059,601 | 10/1991 | Salimbeni | 514/255 |
| 5,290,790 | 3/1994 | Arrang | 514/326 |

FOREIGN PATENT DOCUMENTS

0197840 10/1986 European Pat. Off. .
0494010 7/1992 European Pat. Off. .

OTHER PUBLICATIONS

Tyers "5-HT$_3$ Receptors" Ann. New York, Aca. Sci. 600 194–202 (1990).

Christopher A. Lipinski et al., "Bioisosteric Prototype Design of Biaryl Imidazolyl and Triazolyl Competitive Histamine H$_2$-Receptor Antagonists", J. Med. Chem., vol. 29, No. 11, Nov. 1986.

W. Schunack, "Histaminähnliche Verbindungen mit cyclisierter Seitenkette", Archiv der Pharmazie, vol. 306, No. 12, Dec. 1973.

*Primary Examiner*—Ceila Chang
*Attorney, Agent, or Firm*—Jacobson, Price, Holman & Stern

[57] ABSTRACT

A compound which is a piperidine derivative of formula (I)

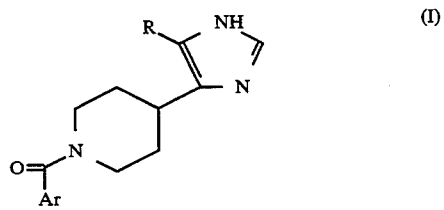

in which
R represents hydrogen, or unbranched or branched C$_1$–C$_6$ alkyl group; and
Ar represents phenyl optionally substituted with one or more radicals selected from the halogens, amino, C$_1$–C$_2$ alkoxy and (C$_3$–C$_6$)cycloalkyl(C$_1$–C$_2$)alkoxy, or a heteroaryl group;
or a pharmaceutically acceptable acid addition salt thereof;
provided that when R is hydrogen Ar is not phenyl or 4-chlorophenyl.

The compounds are useful in therapy as ligands for 5-HT$_3$ and 5-HT$_4$ receptors.

5 Claims, No Drawings

PIPERIDINE DERIVATIVES, THEIR PREPARATION AND THEIR APPLICATION IN THERAPY

The invention relates to piperidine derivatives, to their preparation and their application in therapy.

According to the invention there is provided a compound which is a piperidine derivative of formula (I)

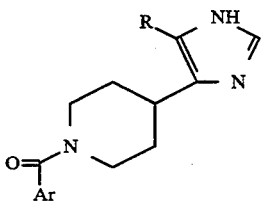

in which
R represents hydrogen, or unbranched or branched $C_1$–$C_6$ alkyl; and
Ar represents phenyl optionally substituted with one or more radicals selected from the halogens, amino, $C_1$–$C_2$ alkoxy and $(C_3$–$C_6)$cycloalkyl$(C_1$–$C_2)$alkoxy, or a heteroaryl group;
or a pharmaceutically acceptable acid addition salt thereof;
provided that when R is hydrogen Ar is not phenyl or 4-chlorophenyl.

When Ar represents substituted phenyl, the number of radicals on the phenyl group is from 0 to 5, preferably 2 or 3.

Preferred compounds of the invention are ones in which Ar represents phenyl optionally substituted with one or more radicals selected from chlorine, amino, methoxy and cyclopropylmethoxy; imidazo[1,2-a]pyridin-2-yl; 3-indolyl; or 3-indazolyl optionally substituted at position 1 with a radical selected from $C_1$–$C_2$ alkyl and aryl$(C_1$–$C_2)$alkyl and at position 5 with a radical selected from hydrogen, the halogens and $C_1$–$C_2$ alkyl.

Particularly preferred compounds are those in which Ar represents 3-indazolyl optionally substituted at position 1 with a radical selected from $C_1$–$C_2$ alkyl and aryl$(C_1$–$C_2)$alkyl and at position 5 with a radical selected from hydrogen, the halogens and $C_1$–$C_2$ alkyl.

The compounds according to the invention can be in the form of free bases or of addition salts with pharmaceutically acceptable acids. The compounds whose formula is a mesomeric form of formula (I) are included in the invention.

EP-A-0 494 010 describes compounds of formula (I) in which R is hydrogen and Ar is phenyl optionally substituted at the para-position with chlorine.

According to the invention, the compounds of formula (I) may be prepared according to the process illustrated in Scheme 1 below:

Scheme 1

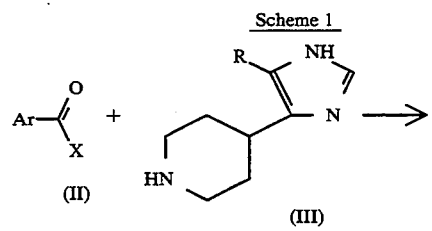

-continued
Scheme 1

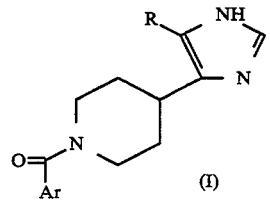

A compound of formula (II) in which Ar is as defined above and X represents a halogen, for example chlorine, or hydroxyl, is reacted with a piperidine derivative of formula (III) in which R is as defined above. The compound of formula (I) thereby produced may be converted into a pharmaceutically acceptable acid addition salt in a known manner.

The starting compounds are commercially available or are described in the literature, or may be prepared according to methods which are described therein or which are known to a person skilled in the art.

1H-Indazole-3-carboxylic acid is described in J. Amer. Chem. Soc., 1952, 2009.

4-Amino-5-chloro-2-(cyclopropylmethoxy)benzoic acid is described in GB-A-1 507 462, GB-A-1 088 581 and GB-A-101 978.

4-(1H-Imidazol-4-yl)piperidine is described in Arch. Pharmaz., (Weinheim. Ger.) 1973, 306(12), 934–42 and in EP-A-0 197 840.

4-(5-Methyl-1H-imidazol-4-yl)pyridine is described. in J. Med. Chem., 1986, 29, 2154–63.

The Examples which follow illustrate in detail the preparation of compounds according to the invention. The structures of the compounds obtained were confirmed by microanalyses and IR and NMR spectra.

EXAMPLE 1

1-(3,5-Dichlorobenzoyl)-4-(1H-imidazol-4-yl)piperidine fumarate 0.469 g (2.5 mmol) of 4-(1H-imidazol-4-yl)piperidine monohydrochloride is dissolved in 5 ml of 1N sodium hydroxide at 0° C. 0.524 g (2.5 mmol) of 3,5-dichlorobenzoyl chloride is then added and the mixture is stirred at 0° C. for 15 minutes. The precipitate obtained is filtered off, washed with 1N sodium hydroxide and then with water and dried. The residue is recrystallized in ethanol.

0.4 g of product are obtained.
Melting point=240°–242° C.

The fumarate is prepared by dissolving the base in ethanol and then adding one equivalent of fumaric acid. The fumarate is recrystallized in a mixture of isopropanol and ethanol.

Melting point=178°–183° C.

EXAMPLE 2

4-(1H-Imidazol-4-yl)-1-[(1H-indol-3-yl)carbonyl]piperidine fumarate 0.81 ml (5.82 mmol) of triethylamine is added to a suspension of 0.48 g (3 mmol) of 1H-indole-3-carboxylic acid and 0.453 g (3 mmol) of 4-(1H-imidazol-4-yl)piperidine in 10 ml of dichloromethane, at room temperature and under argon. 1.29 ml (6 mmol) of diphenylphosphoryl azide are added and the mixture is stirred for 20 hours. The reaction medium is extracted with ethyl acetate in an acid medium. The aqueous phase is recovered, alkalinized with potassium carbonate solution and extracted with ethyl acetate. The organic phase is recovered and washed with water and then with saturated sodium chloride solution. It is dried over magnesium sulphate. The residue obtained is purified by chromatography on a column of silica gel, eluting with a dichloromethane/methanol (90:10) mixture. The pure fractions are evaporated and 0.27 g of product is collected.

To prepare the fumarate, the base is taken up with ethanol and one equivalent of fumaric acid is added. After recrystallization in a mixture of ethanol and isopropyl ether, the product obtained in the form of a hemifumarate is filtered off and dried.

0.3 g of product is obtained.
Melting point=250° C. (dec) Yield=28%

EXAMPLE 3

1-[(1H-Indazol-3-yl)carbonyl]-4-(5-methyl-1H-imidazol-4-yl)piperidine fumarate

In a 100-ml round-bottomed flask, 1.35 g (8.15 mmol) of 4-(5-methyl-1H-imidazol-4-yl)piperidine are placed in 15 ml of dichloromethane and 4 ml of dimethylformamide. 1.32 g (8.15 mmol) of 1H-indazole-3-carboxylic acid and 2.2 ml of triethylamine are added. The mixture is left stirring for 5 minutes. 3.5 ml of diphenylphosphoryl azide are added and the mixture is left stirring for 72 hours. Ethyl acetate is added and the mixture is extracted 3 times with 2N hydrochloric acid. The aqueous phase is recovered and alkalinized with sodium carbonate solution. It is extracted 3 times with ethyl acetate and the organic phase is collected, dried and evaporated to dryness. The residue is purified by chromatography on a column of silica gel, eluting with a dichloromethane/methanol/ammonia solution (90:10:1) mixture.

1 g of product is recovered in the form of the pure base.

The fumarate is prepared as described in Example 1.
Melting point=213°-215° C. Yield=32%

The table which follows illustrates the chemical structures and physical properties of a few compounds according to the invention.

Legend to the table
in the "M.p. (°C.)" column of the table (dec) denotes decomposition
in the "Salt" column of the table (x:y) denotes x mol of acid for y mol of base, the absence of any comment means that the compound is in the state of the base, chlor. represents the hydrochloride fum. represents the fumarate methanesulph. represents the methanesulphonate

TABLE

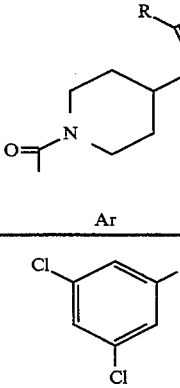

(I)

| No. | R | Ar | M.p. (°C.) | Salt |
|-----|------|------|------------|------|
| 1 | —H | 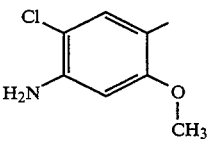 | 178–183 | fum. (1:2) |
| 2 | —H | 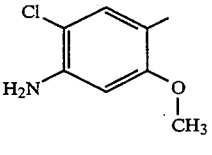 | 140–145 | — |
| 3 | —CH₃ | 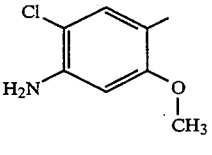 | 135–145 | — |
| 4 | —H | 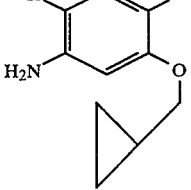 | 135 (dec) | — |

TABLE-continued
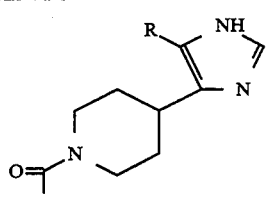
| No. | R | Ar | M.p. (°C.) | Salt |
|---|---|---|---|---|
| 5 | —H | 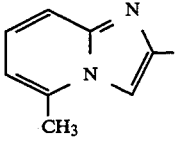 | >220 (dec) | fum. (1:1) |
| 6 | —H | 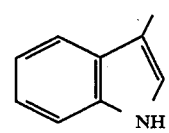 | 220 (dec) | fum. (1:2) |
| 7 | —CH$_3$ | 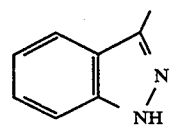 | 175–180 | fum. (1:1) |
| 8 | —H | 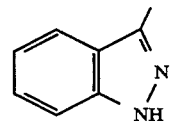 | 210 (dec) | fum. (1:2) |
| 9 | —CH$_3$ | 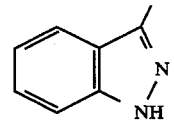 | 202 | — |
| 10 | —CH$_3$ | 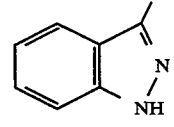 | 213–215 | fum. (1:2) |
| 11 | —CH$_3$ | 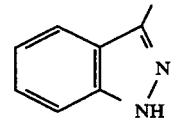 | 235–237 | methanesulph. (1:1) |
| 12 | —(CH$_2$)$_2$CH$_3$ | 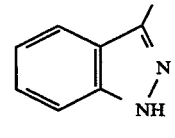 | 217–222 | fum. (1:1) |
| 13 | —CH(CH$_3$)$_2$ | 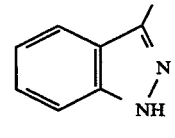 | 239–241 | fum. (1:1) |

TABLE-continued (I) Structure: R and NH-imidazole attached to 4-position of 1-acetylpiperidine, with Ar substituent.

| No. | R | Ar | M.p. (°C.) | Salt |
|---|---|---|---|---|
| 14 | —(CH₂)₃CH₃ | 1H-indazol-3-yl | 220–224 | fum. (1:1) |
| 15 | —H | 5-methyl-1H-indazol-3-yl | 185–192 | fum. (1:1) |
| 16 | —CH₃ | 5-methyl-1H-indazol-3-yl | 186–192 | fum. (1:1) |
| 17 | —H | 5-chloro-1H-indazol-3-yl | 188–195 | fum. (1:1) |
| 18 | —CH₃ | 5-chloro-1H-indazol-3-yl | 206–212 | fum. (1:1) |
| 19 | —(CH₂)₃CH₃ | 5-chloro-1H-indazol-3-yl | 130–135 | chlor. (1:1) |
| 20 | —CH₃ | 1-methyl-1H-indazol-3-yl | 181–182 | — |
| 21 | —CH₂CH₃ | 1-methyl-1H-indazol-3-yl | 182–184 | — |
| 22 | —H | 1,5-dimethyl-1H-indazol-3-yl | 172–175 | fum. (1:1) |

TABLE-continued (I)

| No. | R | Ar | M.p. (°C.) | Salt |
|-----|---|----|------------|------|
| 23 | —(CH₂)₃CH₃ | 5-methyl-1-methyl-indazol-3-yl | 217–220 | — |
| 24 | —H | 5-chloro-1-methyl-indazol-3-yl | 186–192 | fum. (1:1) |
| 25 | —CH₃ | 5-chloro-1-methyl-indazol-3-yl | 218–225 | fum. (1:1) |
| 26 | —(CH₂)₃CH₃ | 5-chloro-1-methyl-indazol-3-yl | >250 | — |
| 27 | —H | 1-benzyl-indazol-3-yl | 165–167 | fum. (1:1) |

The compounds of the invention were subjected to pharmacological tests which showed their value as therapeutically active substances.

Thus, they were tested for their effects on the accummulation of cAMP in a primary culture preparation of neurons of mouse embryo colliculi according to the technique described by Dumuis et al., Mol. Pharmacol., 34, 880–887, 1988. This accummulation reflects adenylcyclase activity to which the type 5-HT₄ serotoninergic receptors are coupled positively.

Colliculi are removed from 14- to 15-day-old mouse embryos. The neurons are separated mechanically and cultured, in 12-well Costar ™ dishes on the basis of 10⁶ cells per well, in a DMEM/F12 ™ nutrient medium with supplements but without serum. The cultures are maintained at 37° C. in a humidified atmosphere (5% CO₂/95% air).

Six days after culturing is started, the cells are incubated for 2 hours in the culture medium described above in the presence of 0.1 nmol of tritiated adenins (specific activity 20 Ci/mmol) per well. The cells are washed with the culture medium and a second incubation is carried out in the culture medium in the presence of isobutylmethylxanthine (0.75 mM), forskolin (0.1 μM) and test products at different concentrations, in a final volume of 1 ml per well. After 10 minutes of incubation, the reaction is stopped by aspirating the medium and adding 1 ml of 5% trichloroacetic acid. The neurons are detached, homogenized using ultrasound and centrifuged at 8000 g for 2.5 minutes. The supernatant is collected and 100 μl of a solution containing cAMP (5 mM) and ATP (5 mM) are added. The tritiated ATP and cAMP formed are separated by passage through DOWEX ™ AG50WX8 resin and then through alumina.

The results were expressed as % [³H]-cAMP/[³H]-ATP

The EC$_{50}$ and IC$_{50}$ values represent, respectively, the concentrations which produce one half of the maximal stimulation and of the maximal inhibition.

The compounds of the invention which are most active in this test are characterized by IC$_{50}$ values of between 1 and 10 μM.

The compounds of the invention were also tested in vivo for their effect on 5-HTP-induced diarrhoea in mice according to the technique described by Warrick et al., J. Pharm. Pharmacol., 33, 675–676, 1981. Male CD$_1$ mice weighing 25–30 g and fasted for 18 hours are used. The compounds or the vehicle is/are administered 20 minutes (intraperitoneal route) or 60 minutes (oral route) before the intraperitoneal injection of 5-HTP at a dose of 25 mg/kg. The animals are placed in individual cages and are observed for 3 hours, noting the number of animals having diarrhoea 30 minutes, 1 hour, 2 hours and 3 hours after the administration of 5-HTP.

The results are expressed as a percentage of animals protected by the pretreatment in comparison to the control animals which have received the vehicle as a pretreatment.

The compounds of the invention which are most active An this test inhibit 5-HTP-induced diarrhoea after a dose of 0.002 mg/kg administered intraperitoneally or 0.1 mg/kg administered orally.

The compounds according to the invention were also tested for their inhibitory effects on the binding of [³H]quipazine to the type 5-HT$_3$ serotoninergic receptors present in the rat cerebral cortex, according to a variant of the method described by Milburn and Peroutka (J. Neurochem., 52, 1787–1792, 1989).

Male Sprague-Dawley rats weighing 150 to 200 g are used in all the tests. Their cerebral cortex is removed and homogenized in 20 volumes (weight/volume) of 25 mM Hepes buffer or of 25 mM Hepes buffer containing sodium chloride (180 mM), calcium chloride (2.5 mM), potassium chloride (5 mM) and magnesium chloride (1.2 mM) (pH 7.4) using a Polytron ™ mill. After centrifugation of the suspension for 10 minutes at 45,000×g, the pellet is resuspended in the initial volume of buffer, where appropriate containing 0.05% of Triton X-100 ™, and a first incubation is performed for 30 minutes at 37° C. Two further centrifugations are then performed as described above, and the final pellet is taken up in 11.7 volumes of 25 mM Hepes buffer, pH 7.4.

The binding of [³H]quipazine (51.6–69.8 Ci/mmol, New England Nuclear, Boston, Mass., USA) is determined by incubating 150 μl of the membrane suspension with the radioligand (0.8 nM) in a final volume of 1 ml for 30 minutes at 25° C., in the absence or presence of the compound under study. Incubation takes place in the presence of 0.1 μM paroxetine and 1 μM ketanserin. Non-specific binding is determined in the presence of 1 μM ondansetron. After incubation, the test mixture is diluted with 5 ml of ice-cold 50 mM Tris-HCl buffer (pH 7.4 at 0° C.). The membranes are collected by filtration on Whatman GF/B ™ filters pretreated with 0.05% of polyethylenimine, and washed with three volumes of 5 ml of ice-cold 50 mM Tris-HCl buffer.

The radioactivity retained on the filters is measured by liquid scintillation spectrometry at an efficiency of 50 to 60%.

The results are expressed as the concentration (IC$_{50}$) of the compound under study which inhibits 50% of the binding of [³H]quipazine, determined by a graphic or mathematical method. The compounds of the invention which are most active in this test are characterized by IC$_{50}$ values below 1 nM (10$^{-9}$M).

The results of the biological tests show that the compounds of the invention are ligands for types 5-HT$_3$ and 5-HT$_4$ serotoninergic receptors.

They may hence be used for the treatment and prevention of disorders in which 5-HT$_3$ and 5-HT$_4$ receptors are involved, such as nausea and vomiting, for example following antitumour treatment or the administration of an anaesthetic; disorders of the central nervous system such as schizophrenia, mania, anxiety and depression; disorders of cognition such as senile dementia or Alzheimer's prosenile dementia; dyskinesia, pain, migraine and headache; disorders associated with alcohol or drug dependence or withdrawal; disorders of gastro intestinal function such as dyspepsia, peptic ulcer, heartburn, flatulence; disorders of the cardiovascular system and respiratory disorders.

They may also be used for the treatment and prevention of disorders such as diarrhoea, irritable colon, oesophageal reflux, intestinal motor function disorders, disorders of intestinal secretion, cystic fibrosis of the pancreas, carcinoid syndrome and incontinence.

For this purpose, they may be presented in all forms suitable for oral or parenteral administration, such as tablets, dragées, capsules including hard gelatin capsules, suspensions or solutions to be swallowed or injected, and the like, in combination with suitable excipients, and in doses that enable 0.005 to 10 mg to be administered 1 to 4 times a day.

We claim:

1. A compound of formula (I)

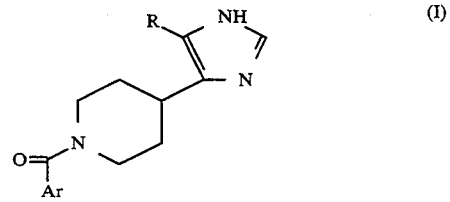

in which
R represents hydrogen, or unbranched or branched C$_1$–C$_6$ alkyl; and
Ar represents phenyl optionally substituted with one or more radicals selected from the group consisting of the halogens, amino, C$_1$–C$_2$ alkoxy and (C$_3$–C$_6$-)cycloalkyl(C$_1$–C$_2$)alkoxy, imidazo[1,2-a]pyridin-2-yl; 3-indolyl; or 3-indazolyl optionally substituted at position 1 with a radical selected from the group consisting of C$_1$–C$_2$ alkyl and aryl(C$_1$–C$_2$)alkyl and at position 5 with a radical selected from the group consisting of hydrogen, the halogens and (C$_1$–C$_2$)alkyl;

or a pharmaceutically acceptable acid addition salt thereof; provided that when R is hydrogen Ar is not phenyl or 4-halophenyl.

2. A compound according to claim 1, wherein Ar represents phenyl optionally substituted with one or more radicals selected from the group consisting of chlorine, amino, methoxy and cyclopropylmethoxy; imidazo[1,2-a]pyridin-2-yl; 3-indolyl; or 3-indazolyl optionally substituted at position 1 with a radical selected from the group consisting of $C_1$-$C_2$ alkyl and aryl($C_1$-$C_2$)alkyl and at position 5 with a radical selected from the group consisting of hydrogen, the halogens and ($C_1$-$C_2$)alkyl.

3. A compound of formula (I)

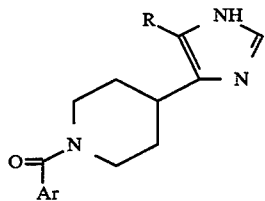

(I)

in which

R represents hydrogen, or unbranched or branched $C_1$-$C_6$ alkyl; and characterized in that Ar represents a 3-indazolyl group optionally substituted at position 1 with a radical chosen from ($C_1$-$C_2$)alkyl and phenyl ($C_1$-$C_2$)alkyl groups and at position 5 with a radical chosen from hydrogen and halogen atoms and the ($C_1$-$C_2$)alkyl group.

4. A pharmaceutical composition comprising a compound as claimed in claim 1 or 2 and a pharmaceutically acceptable excipient.

5. A method for treating or preventing nausea, vomiting, a disorder of gastrointestinal function selected from diarrhoea, irritable colon, oesophageal reflux, an intestinal motor function disorder and a disorder of intestinal secretion, or incontinence.

* * * * *